United States Patent [19]
Schimenti et al.

[11] Patent Number: 5,994,620
[45] Date of Patent: Nov. 30, 1999

[54] INDUCED CHROMOSOMAL DELETION

[75] Inventors: John Schimenti; Yun You, both of Bar Harbor, Me.

[73] Assignee: The Jackson Laboratory, Bar Harbor, Me.

[21] Appl. No.: 08/763,048

[22] Filed: Dec. 10, 1996

[51] Int. Cl.⁶ .................................................. C12N 15/00
[52] U.S. Cl. .............................. 800/25; 800/21; 435/446; 435/463
[58] Field of Search .................................. 435/172.3, 325, 435/255.1; 800/2, DIG. 1

[56] References Cited

U.S. PATENT DOCUMENTS 4,959,317  9/1990  Saner .................................... 435/172.3

OTHER PUBLICATIONS

D Strauss et al (1990) Proc Natl Acad Sci USA 87: 1889–1893.
KR Peterson et al (1995) Proc Natl Acad Sci USA 92: 5655–5659.
Rp Woychik et al (1990) Proc Natl Acad Sci USA 87: 2588–2592.
BM Cattanach et al (1993) Nature Genetics 3: 56–61.
JH van Doorninck et al (1995) EMBO J 14: 4403–4411.
M Serwe et al (1993) EMBO J 12: 2321–2327.
Russell et al., *Genetics 100*: 427–453 (1982).
Holdener–Kenny et al., *Bioessays 14*: 831–839 (1992).
Ramirez Solis et al., *Nature 378*: 720–724 (1995).
Urlaub et al., *Som. Cell. Mol. Genetics 12*: 555–566 (1986).
Kavathas et al., *Proc. Nat. Acad. Sci. USA 77*: 4251–4255 (1980).
Riele et al., *Proc. Nat. Acad. Sci. USA 89*: 5128–5132 (1992).
Rinchik et al., *Genetics 137*: 845–854 (1994).
Russell, *Cold Spring Harbor Symp. Quant. Biol. 16*: 327–336 (1951).

*Primary Examiner*—Bruce R. Campell
*Attorney, Agent, or Firm*—Kevin M. Farrell

[57] ABSTRACT

Disclosed is a method for the production of deletions in the chromosomal DNA of a single eukaryotic cell. More specifically, the method involves the creation of either random chromosomal deletions, or chromosomal deletions within a predetermined genetic loci. The deletions are created by integration of a DNA construct into the chromosomal DNA of the single eukaryotic cell, followed by spontaneous or irradiation induced deletion of the DNA construct from the chromosomal DNA. Also, disclosed is a method for the production of deletions in the chromosomal DNA of a multicell organism using a DNA construct.

8 Claims, No Drawings

INDUCED CHROMOSOMAL DELETION

BACKGROUND OF THE INVENTION

Deletions are entire regions of chromosomes that are no longer present in the genome. Chromosomal deletions are powerful tools in the genetic analysis of complex genomes. They have been exploited extensively in several species including *Drosophila melanogaster*, humans and mice. *Drosophila melanogaster* is an organism in which deletions in the genome can be efficiently induced and selected. Chromosomal deletions in the genome of *Drosophila melanogaster* can be induced through the use of either irradiation or treatment with a mutagenic chemical. In humans, deletions that have arisen spontaneously have facilitated the dissection of phenotypes in contiguous gene syndromes. The identification of deletions in the genome of humans has led to the positional cloning of genes with functions critical to the normal functions of the individual. In mice, sets of deletions within particular regions of the genome created by whole animal irradiation experiments have enabled a systematic characterization of functional units along defined chromosomal regions. However, due to the inordinate amount of time required to identify sets of unique deletions within a particular predetermined genetic locus, classical mutagenesis in mice is logistically impractical.

Presently, the most efficient method that can be used to create a chromosomal deletion at a predetermined genetic locus in mice is the Cre/loxP system disclosed in the U.S. Pat. No. 4,959,317. This recombination system uses two DNA constructs that are integrated into predetermined genetic loci on a chromosome, thus enabling the generation of a precise, single deletion in between the two inserted constructs. When a chromosomal deletion is desired in the genome of a mouse, the deletion is first created in an ES (embryonic stem) cell. The ES cell is then injected into a murine multicell blastocyst or morula or aggregated to an earlier stage murine embryo. ES cells used in this manner have the ability of developing into a chimeric mouse which contains the predetermined chromosomal deletion. The Cre/loxP recombination system however, lacks the feature of creating sets of unique deletions at a predetermined genetic locus afforded by classical mutagenesis. In order to create these sets using the Cre/loxP system, it is necessary to produce two new DNA constructs for each desired deletion. Therefore, the Cre/loxP system requires a great deal of effort and time in order to create sets of unique deletions within a predetermined genetic region.

SUMMARY OF THE INVENTION

The invention relates in one aspect to a method for producing deletions in the chromosomal DNA of a eukaryotic cell. The method involves introducing into the eukaryotic cell a DNA construct containing either a selectable marker gene or a selectable marker gene flanked on its 5' and 3' ends with DNA sequences which are complementary to a predetermined target site. The DNA construct has the capability of integrating into the chromosomal DNA by homologous recombination. Eukaryotic cells that undergo recombination are able to delete at least a portion of the DNA construct either through a spontaneous deletion event or following irradiation.

In another aspect, the present invention relates to a method for producing deletions in the chromosomal DNA of a eukaryotic cell which can be used to generate a viable multicell organism. The method involves introducing into the cell a DNA construct containing either a selectable marker gene or a selectable marker gene flanked on its 5' and 3' ends with DNA sequences which are complementary to a predetermined target site. The DNA construct has the capability of integrating into the chromosomal DNA by homologous recombination. Eukaryotic cells that undergo recombination are able to delete at least a portion of the DNA construct either through a spontaneous deletion event or following irradiation. Those eukaryotic cells that delete at least a portion of the DNA construct are selected for insertion into a multicell blastocyst or morula or are aggregated to an earlier stage embryo, thereby creating a chimeric multicell embryo. The chimeric multicell embryo is incubated under conditions appropriate for development into a viable chimeric multicell organism. The chimeric multicell organism is screened for deletion of at least a portion of the DNA construct.

In another aspect, the invention relates to a chimeric multicell organism developed from a chimeric multicell embryo consisting of an embryonic stem cell containing a chromosomal deletion and a multicell blastocyst, morula or earlier stage embryo. The chromosomal deletion is created by introducing into the eukaryotic cell a DNA construct containing either a selectable marker gene or a selectable marker gene flanked on its 5' and 3' ends with DNA sequences which are complementary to a predetermined target site. The DNA construct has the capability of integrating into the chromosomal DNA during recombination. Eukaryotic cells that undergo recombination are able to delete at least a portion of the DNA construct either through a spontaneous deletion event or following irradiation.

DETAILED DESCRIPTION OF THE INVENTION

The present invention is based, in one aspect, on a method for the production of sets of nested deletions within a genetic locus of a complex genome in a eukaryotic cell. The nested deletions occur either spontaneously or following irradiation. The method relies on the integration of a DNA construct into a chromosome through recombination. The DNA construct contains either a selectable marker gene or a selectable marker gene flanked on its 5' and 3' ends with DNA fragments which are complementary to a predetermined chromosomal target site. Following either a spontaneous deletion or irradiation, at least a portion of the DNA construct at the site of integration is deleted. The spontaneous deletion frequency is low, while irradiation induces deletion at a rate which is proportional to the amount of irradiation the eukaryotic cells are exposed to.

The eukaryotic cell can be either a single cell organism or an embryonic stem cell. In the present invention, an embryonic stem cell encompasses those cells which when injected into a multicell blastocyst or morula or aggregated to an earlier stage embryo are capable of generating, following an appropriate incubation period, a multicell organism. As disclosed in the Exemplification section which follows, the site at which the DNA construct integrates does not have to be very well characterized. For the present invention to work no DNA sequence data or extensive restriction enzyme mapping is necessary.

Deletions which result in entire regions of chromosomes being removed can be used to carry out genetic analysis of complex genomes. Presently, methods to induce unique sets of deletions in an animal involve either irradiation of the entire animal or treatment of the entire animal with a chemical mutagen. These methods induce chromosomal deletions in a random manner, with identification of a desired deletion within a particular genetic locus restricted to regions affecting a visible characteristic.

Recently, a more efficient technique was developed which can be used to target deletions to a particular locus within the genome. This method is taught in U.S. Pat. No. 4,959,317, which discloses the use of the Cre/loxP system. Using Cre-loxP, deletions can be targeted to a predetermined site within the genome. However, the Cre/loxP system has limitations which include the ability to create only one deletion at the predetermined genomic locus for each pair of DNA constructs that are utilized.

The present invention overcomes the inability to efficiently create sets of unique deletions at a predetermined genetic locus experienced when using the Cre/loxP system. In the present invention, by creating a single DNA construct which does not need to be well characterized, production of comprehensive sets of nested deletions can be created at a genetic locus. The experiments described in the following section demonstrated, for example, that a set of unique deletions of various lengths covering different regions of a predetermined chromosomal region could be created and screened in a short period of time. Although the bulk of the in vivo data reported herein were generated in experiments employing a murine model system, the fundamental principles are applicable to other multicell organisms as well as individual eukaryotic cells. The present invention relates in one embodiment to methods for the creation of nested sets of deletions within a chromosomal location of a single eukaryotic cell. A commonly studied eukaryotic single cell organism is *Saccharomyces cerevasiae*, more commonly known as yeast. In order to create the deletion sets, a DNA construct capable of successfully integrating into the genome during a recombination event is created. The DNA construct itself can take on various forms; for example a plasmid as described in the Exemplification section below.

The components of the DNA construct are chosen based on whether integration is to occur randomly throughout the genome or at a predetermined genetic loci. When the integration is to occur at a random, not at a predetermined site in the genome, the DNA construct contains a selectable marker gene. Once this DNA construct integrates into the chromosomal DNA, the genome is screened to both identify the genomic location of the DNA construct and determine whether this genetic locus is of interest. When the site of integration is targeted to a predetermined genetic locus, the DNA construct contains a selectable marker gene which is flanked on both its 5' and 3' ends by portions of genomic DNA known as DNA fragments. These DNA fragments have homology with the predetermined genetic locus in the chromosome at which integration is desired.

The set of selectable marker genes that can be part of the DNA construct include the following genes and the lethal chemical compounds used to screen for their presence: the Herpes Simplex Virus thymidine kinase gene which confers sensitivity to FIAU and gangcyclovir; the neomycin phosphotransferase gene which confers resistance to the drug gentamicin or G418; the hygromycin B phosphotransferase gene which confers resistance to hygromycin; 0-Demethylpuromycin 0-Methyltransferase gene which confers resistance to puromycin; and hypoxanthine-guanine phosphoribosyl transferase gene which confers resistance to azaserine, aminopterin and methotrexate and sensitivity to 6-thioguanine. Those selectable marker genes not included in the preceding group that would function as a selectable marker gene as part of a DNA construct are also included within the scope of present invention.

The selectable marker genes present in the DNA construct can be used individually or in groups of two or more unique genes. One class of selectable marker genes are those which kill a cell (e.g., Thymidine Kinase) in the presence of a certain chemical (e.g., FIAU or gancyclovir). In choosing a selectable marker gene, it is important to ensure that the gene is not endogenous to the cell of interest.

The selectable marker genes can be assayed by the addition of a lethal chemical compound to the media in which the cells are propagated. For instance, the neomycin resistance gene, when present in a cell and actively transcribed, protects the cell when it is grown in media containing G418. Those cells which lack the neomycin resistance gene do not survive. In the present invention the resultant pool of surviving cells include those that contain the selectable marker genes.

The DNA fragment which has homology to the targeted predetermined genetic locus does not have to be well characterized. For example, the DNA fragment contained in the DNA construct can be uncharacterized with respect to nucleotide sequence and restriction enzyme digestion pattern. The DNA fragment itself can come from a cloned piece of genomic DNA that is contained in a cosmid, a lambda vector, a YAC vector or another type of DNA vector. These DNA vectors are useful since it is relatively easy to excise a DNA fragment from them using a restriction enzyme after which the DNA fragment can be isolated, purified, and cloned into the DNA construct of the present invention. The combined length of the two DNA fragments that constitute the homologous genomic DNA of the DNA construct of the present invention can vary. The optimum length of the two combined DNA fragments falls in the range of 5–15 kilobases (kb).

The DNA constructs described herein can be inserted into the eukaryotic cell by transformation methods known to one of skill in the art. Such methods include, for example, electroporation of the DNA construct into a cell. Not every cell that has gone through the transformation protocol will harbor a copy or multiple copies of either of the DNA constructs. In addition, not every cell transformed with either of the DNA construct will integrate said constructs into the chromosome. Therefore, at least two different screening techniques are necessary to identify those cells which have successfully integrated the DNA construct.

The present invention further involves methods to screen eukaryotic cells to determine whether the DNA construct the eukaryotic cell was transformed with has successfully integrated into the chromosome at the predetermined genetic locus. The first means of screening eukaryotic cells following transformation involves exposing the eukaryotic cells to the lethal chemical compound which the selectable marker gene in the DNA construct confers protection against. Those eukaryotic cells actively expressing the selectable marker gene will be protected from the lethal effects of the chemical compound. Those eukaryotic cells which do not contain the selectable marker gene will not survive the addition of the lethal chemical compound to the media. Thus, surviving eukaryotic cells will contain at least one copy of the selectable marker. However, not all of the surviving eukaryotic cells will have successfully integrated the DNA construct into their genome.

For confirmation that the DNA construct has successfully integrated into the chromosome during recombination, the genomic DNA of the eukaryotic cells is processed by a means that allows visualization of the selectable marker gene only if it is successfully integrated into the chromosome. This method involves the isolation and purification of genomic DNA from the eukaryotic cell in a manner that ensures that no extrachromosomal DNA elements are present. This can be accomplished using standard genomic DNA isolation protocols. Isolated genomic DNA is cut with a restriction enzyme, electrophoresed through an agarose or polyacrylamide gel, transferred onto a solid support (e.g., a nitrocellulose or a nylon filter) and probed with labeled DNA probes specific for chromosomal sequences flanking the DNA construct. Only those eukaryotic cells that are shown to have successfully integrated the selectable marker into the genome are propagated for further manipulation.

The present invention further includes methods for the deletion of the DNA construct from the site of integration. In one embodiment, the chromosomal deletion occurs spontaneously in cultured eukaryotic cells. To identify a spontaneous deletion, wherein at least a portion of the integrated DNA construct containing a selectable marker gene is lost, the eukaryotic cells are propagated in culture media to a number of at least $1 \times 10^7$ eukaryotic cells. This is the minimum number of eukaryotic cells necessary to ensure the detection of at least one eukaryotic cell with a spontaneous chromosomal deletion. The actual deletion rate is very low, approximately 1/200,00. Therefore, the chance that a single eukaryotic cell will have more than one deletion is extremely rare.

In a second embodiment, the chromosomal deletion is induced by irradiation of eukaryotic cells which have successfully integrated the DNA construct containing the selectable marker gene and flanking DNA fragments with homology to the predetermined genetic locus. Prior to irradiation, these eukaryotic cells are expanded in the appropriate growth medium to a number of at least $1 \times 10^6$ eukaryotic cells. This is the minimum number of eukaryotic cells necessary to ensure the detection of at least one eukaryotic cell with a chromosomal deletion. When a sufficient number of eukaryotic cells are obtained, they are exposed to an irradiation source. One example of a source that is commonly used to irradiate cells is $^{137}Cs$. However, those of skill in the art will recognize that other irradiation sources will also work in the present invention.

The amount of time eukaryotic cells are exposed to the irradiation source can vary based on strength of the source and resistance of the eukaryotic cells to irradiation induced deletions. In general, cells are exposed to 400 RADS of irradiation. This amount of irradiation has been shown to consistently yield a sufficient number of eukaryotic cells which have both lost the selectable marker by deletion from the chromosome and can be identified by the aforementioned screening methods. The actual deletion rate found in eukaryotic cells following irradiation is extremely low. On average, only about 1 out of every 20,000 eukaryotic cells deletes a portion of the chromosomal DNA at the predetermined genetic locus. Therefore, the chance that a single eukaryotic cell will ever have more than one deletion of chromosomal DNA in its genome is very rare.

Screening of eukaryotic cells that have lost the selectable marker gene can be accomplished by selection in the appropriate culture medium. The first step involves the identification of eukaryotic cells that are resistant to the lethal effects of a chemical compound that kills cells that still possess the selectable marker gene. Those eukaryotic cells that survive following addition of the lethal chemical compound to the growth media are next screened for the physical loss of the selectable marker gene from the genomic DNA. The genomic DNA of the eukaryotic cell is processed and examined as described above. This can include, for example, restriction enzyme digestion, electrophoresis through either an agarose or polyacrylamide gel, southern blotting onto a solid support and probing with a labeled DNA probe specific for the selectable marker. Loss of flanking markers can be rapidly detected by using PCR to type polymorphic, linked microsatellite markers.

Sets of unique deletions are created in eukaryotic cells which have deleted a portion of the DNA construct through either a spontaneous deletion or irradiation induced deletion. The number of deletions will vary with each set of eukaryotic cells that undergo either a spontaneous or irradiation induced deletion. However, by repeating the deletion method taught by the present invention multiple times, it is possible to produce hundreds of nested deletions within a genetic locus.

In another aspect of the present invention, nested deletion sets are created within the genetic loci of eukaryotic cells known as embryonic stem cells. Embryonic stem cells are characterized by their ability to create a chimeric multicell organism after they have been injected into a multicell blastocyst or morula or aggregated to an earlier stage embryo. The most well studied of this type of cell is the embryonic stem (ES) cell lines that have been used to create chimeric mice. In recent years, the ES cell lines have been used to create chimeric mice which contain a gene or sets of genes which were altered in a manner such that the gene loses its ability to function properly. This has been termed "knocking out" a gene and the mice containing this trait have been called "knockout mice".

Deletions in murine ES cells can be created in a manner similar to that described above for eukaryotic single cell organisms. The methods used include the transformation of murine ES cells with a DNA construct containing either a selectable marker gene or a selectable marker gene flanked on both its' 5' and 3' ends with DNA fragments that are complementary to the desired site of integration.

The DNA construct containing the selectable marker gene is capable of randomly integrating into chromosomal DNA. The genetic loci that this DNA construct integrates is not predetermined, but is identified following the recombination of the DNA construct into the chromosome. For targeting a DNA construct to a predetermined site of integration the optimum combined total length of the two DNA fragments falls in the range of 5–15 kb. This DNA construct integrates into the genomic DNA at a predetermined genetic locus through homologous recombination.

Following transformation, murine ES cells are screened for the presence of the selectable marker gene within the genome as described above. Next, murine ES cells carrying the integrated selectable marker gene are cultured and selected for a spontaneous mutation or irradiated to induce a mutation. These murine ES cells are screened for loss of the selectable marker gene by methods described above. At this point, murine ES cells which have deleted the selectable marker gene are injected into a viable multicell murine blastocyst or morula or aggregated to an earlier stage embryo to create a chimeric multicell murine embryo. Injection of murine ES cells is accomplished using a micromanipulator apparatus by techniques known to one of skill in the art. The chimeric multicell murine embryo is inserted into the uterus of a female mouse where after an appropriate incubation period it develops into a fully formed chimeric mouse pup. Chimeric mouse pups are usually visualized on the basis of coat color differences encoded within the genomes of the host blastocyst, morula or earlier stage embryo and the injected ES cells. They are also detected by isolation of DNA from the offspring, followed by PCR analysis of polymorphic loci in the genetic region within which the DNA construct integrated. Chimeric mouse pups can also be detected by restriction enzyme digestion, electrophoresis in an agarose or polyacrylamide gel, Southern blotting of the gel onto a solid support, and probing with a labeled probe specific for a loci contained within the deletion.

If the deletion is present in the germ cells of a chimeric mouse, either sperm or egg, it is possible to create offspring that are homozygous for the deletion at the predetermined genetic locus. Those of skill in the art will recognize that the present invention is not limited to the creation of chimeric mice and their offspring. Other chimeric multicell organisms or their homozygous offspring can be prepared by the methods disclosed above.

Creation of chimeric mice or their homozygous offspring or other chimeric multicell organisms or their offspring that contain a unique chromosomal deletion within a predetermined genetic locus, will aid in the study of gene function in mammals and other multicell organisms. By use of the methods disclosed in the present invention, it is possible to identify genes that are involved in various cellular functions, many of which may be critical to the survival of both eukaryotic single cell organisms and multicell organisms.

In addition, to the uses discussed above, the present invention finds application for example, in recombinant protein production. The production of pure nonendogenous recombinant proteins in eukaryotic cells grown in vitro is an economical and efficient means to produce large quantities of a desired gene product. However, in several instances, the synthesis of nonendogenous recombinant proteins in vitro by eukaryotic cells has been found to have detrimental side-effects. Included among these are the death of the eukaryotic cells or prevention of further division by the eukaryotic cells. The present invention overcomes these obstacles by allowing the production of nonendogenous recombinant proteins only after the eukaryotic cell density reaches a level at which further eukaryotic cell growth is not required.

In the present invention, the gene used to produce the nonendogenous recombinant protein is placed under the control of a distal regulatory gene which prevents transcription of the nonendogenous recombinant gene. In order to express the nonendogenous recombinant gene, the regulatory gene needs to be inactivated. In the present invention this involves the deletion of the regulatory gene from the chromosome.

Deletion of the regulatory gene is accomplished by a method that involves first, the recombination of a DNA construct into the chromosomal DNA encoding the regulatory gene. This is followed by the irradiation induced deletion of the regulatory gene from its chromosomal DNA location. To accomplish this method, the eukaryotic cells are transformed with a DNA construct which contains a selectable marker flanked on both its 5' and 3' ends with DNA fragments which are complementary to the regulatory gene. Following transformation, the DNA construct integrates into the chromosomal DNA of the regulatory gene through homologous recombination. Following recombination, the eukaryotic cells are irradiated, which results in the deletion of the regulatory gene from the chromosome. With removal of the regulatory gene complete, the nonendogenous recombinant protein can be produced without concern for adverse effects on the growth or long term viability of the eukaryotic cells.

The selectable marker of the DNA construct is used to identify the percentage of eukaryotic cells which are transformed with the DNA construct. The first step involves growing the eukaryotic cells in the presence of the lethal chemical compound the selectable marker confers resistance to. The percentage of cells which survive cultivation in the presence of the lethal chemical compound is determined. Thus, the transformation process described above can be optimized such that the amount of DNA construct added to the eukaryotic cells is able to effectively transform all the eukaryotic cells and maximize the yield of the pure nonendogenous recombinant protein.

EXEMPLIFICATION

Disclosed in this Exemplification section is a method for the generation of radiation-induced sets of nested deletions within a defined region of the murine genome. The method utilizes ES cells, and a DNA construct containing a selectable marker flanked on both sides by DNA fragments from the locus of interest. The DNA construct is inserted into the genomic DNA of the ES cell at the site of the desired locus through homologous recombination. One feature of the present invention is that the locus of interest does not have to be well characterized in order to create a set of deletions. Following confirmation of integration of the selectable marker into the genome, ES cells are irradiated and selected for both loss of the selectable marker and DNA deletion. Dozens of different deletions that encompass a specific locus, some overlapping other deletions, can be created within ES cells in a single experiment. Deletions can vary in size, with the largest ones spanning several centiMorgans. In the experiments described below, these deletions were transmitted from the chimeric mice to their pups through the germline. This ability to rapidly create and maintain deletion complexes within a particular locus will facilitate systematic functional analyses of the mammalian genome.

Methods

ES cells and Radiation

A suspension of ES cells was divided into five equal parts and exposed to 0, 100, 200, 300, or 400 RADS of radiation from a $^{137}$Cs source. A portion of each sample was then seeded at low density onto feeder plates, and resulting colonies counted to generate kill curves. The remainder of each sample was expanded, and about 10 cells were injected into C57BL/6J blastocysts. Isolation of the 129/Sv agouti CJ7 cells has been described (Swiatek, P. J. & Gridley, T., *Genes Dev* 7: 2071–2084 (1993)). The stock of cells used in these experiments was actually a germline-competent subclone. The v17.2 ES cell line was derived from blastocysts obtained in matings of BALB/cJ females to 129/SC$^{Jae}$ males. All three lines are XY. ES cells were grown on mitotically inactivated mouse embryonic fibroblasts in the presence of LIF (Leukemia Inhibitory Factor).

Targeting into the D17Aus9 Locus

Two plasmids for a generic targeting scheme were created. pSKΔBam is a derivative of pBluescript in which the BamHI site was destroyed by digestion and Klenow filling. The plasmid pBAN/tKBcs contains tandemly arranged TK and neo genes, each with their own promoter, inserted into pBluescript such that they are excisable as a BamHI fragment. The D17Aus9 targeting vector was built by isolation of a 129/Sv lambda Fix clone, subcloning of a 9 kb EcoRI fragment into pSKΔBam, and ligating the TK/neo cassette into a unique BamHI site in the 9 kb insert. Following electroporation, targeted clones were recovered at a rate of about 10% of G418-resistant ES cell clones.

Characterization of Deletions

Numerous microsatellite loci were typed to identify polymorphisms between BALB/cJ and 129 as described (Dietrich et al., Nature Genet. 7: 220–245 (1994)). T alleles were typed by RFLP analysis; BALB/cJ and 129/Sv differ in TaqI fragments detected by a cDNA probe for T. The D17Aus9 probe is a fragment 10 kb downstream of the TK/neo integration site that also detects a TaqI RFLP.

Selection of Deleted Clones

Targeted ES cells were grown in G418 until irradiation. $9.5 \times 10^7$ and $0.5 \times 10^7$ cells were exposed to 400 and 0 RADS respectively, and plated at a density of 1000 cells/mm$^2$ (400 RAD) or 300 cells/mm$^2$ (no irradiation) onto gelatin-coated plates in the presence of LIF. Selection at higher densities, or in the presence of feeders, resulted in death of genetically TK deficient cells. 0.2 mM 1-2'-deoxy-2'-fluoro-β-D-arabinofuranosyl-5-iodouracil (FIAU) selection was applied 48 hours after irradiation, for 4 days. Colonies were picked about 5 days later.

Results and Discussion

Ionizing radiation is known to induce large deletions in cultured mammalian cells. To explore the feasibility of using ES cells for generating interstitial deletions in mice, the effects of γ-irradiation on the developmental potential of three genotypes of ES cells was investigated: 129, BALB/c, and (BALB/c×129) F1. Each genotype displayed similar levels of lethality from 100–400 RADS of γ-irradiation. Surviving cells at each exposure level were injected into blastocysts to generate chimeras. The ability of 129 ES cells to form chimeric mice with germline contribution was reduced with as little as 100 RADS of γ-irradiation, and almost completely eliminated with 300–400 RADS.

The contrasting results between genotypes indicate that radiation induces a permanent alteration in the developmental capacity of 129 ES cells, but heterozygosity for the BALB/c genome somehow prevents this effect. BALB/c cells treated with 400 RADS of radiation retained the ability to create germline chimeras, suggesting that genes from this strain provide dominant rescue of the susceptibility in 129 ES cells. It is possible that the 129 ES cells are inferior in some aspect of DNA repair that results in compromised developmental potential, but not cell viability.

The strategy for the creation of a deletion complex consists of three steps: 1) integration of a negatively selectable marker into a predetermined locus by homologous recombination, (in the present specification the Herpes Simplex Virus thymidine kinase gene (TK) was used); 2) treatment of targeted cells with radiation and selection for loss of TK expression with the drug FIAU; and 3) genotyping TK$^{31}$ clones for the presence or absence of polymorphic flanking markers. A primary feature of this experimental paradigm is that the targeting step requires minimal characterization of the locus around which deletions are to be made. A prior knowledge of chromosomal orientation or genes in the area is not required. Steps 2 and 3 are feasible in F1 hybrid ES cells due to their radiation tolerance and allelic polymorphism. These cells also enable preferential integration of the TK marker into either the maternal or paternal chromosome by using isogenic targeting constructs. This is a consideration when generating deletion complexes on chromosomes known to contain imprinted genes.

TABLE 1

Effects of Radiation on Developmental Potential of ES cells.

| Cell line | Rads | # Blast. Inj. | Born | % Chim. | Chimerism >80% + <80% | Male Germline |
|---|---|---|---|---|---|---|
| CJ7 (129/Sv) | 0 | 64 | 16 | 69 | 10 ± 1 | 7/7 (100%) |
|  | 100 | 86 | 31 | 45 | 7 + 7 | 4/10 (40%) |
|  | 200 | 45 | 12 | 33 | 1 + 3 | 1/4 (25%) |
|  | 300 | 30 | 7 | 29 | 0 ± 2 | 0/2 (0%) |
|  | 400 | 33 | 13 | 8 | 0 + 1 | 0/1 (0%) |
| BALB/c | 0 | 139 | 11 | 64 | 7 + 0 | 3/7 (43%) |
|  | 100 | 30 | 10 | 10 | 1 + 0 | 1/1 (100%) |
|  | 200 | 105 | 37 | 14 | 4 + 1 | 4/5 (80%) |
|  | 300 | 84 | 32 | 8 | 2 + 2 | 1/4 (25%) |
|  | 400 | 95 | 58 | 17 | 2 + 8 | 4/10 (40%) |
| v17.2 (BALB × 129) | 0 | 48 | 7 | 86 | 6 + 0 | 6/6 (100%) |
|  | 100 | 78 | 25 | 52 | 11 + 2 | 5/7 (62.5%) |
|  | 200 | 30 | 8 | 75 | 6 + 0 | 6/6 )100%) |
|  | 300 | 62 | 20 | 70 | 14 + 0 | 10/12 (83%) |
|  | 400 | 50 | 12 | 92 | 11 + 0 | 9/9 (100%) |

LEGEND. The cells injected into blastocysts were survivors from the kill curve experiment shown in FIG. 1 "# Blast. Inj." refers to the number if C57BL/6J blastocysts injected, and the "Born" column lists the number of pups weaned from those injections. "% Chim." is the percentage of all animals derived from the injections that showed any evidence of coat color chimerism. Chimeras were ranked into 2 categories: greater or lesser than 80% agouti. The absolute numbers in each class at each radiation exposure listed in the "Chimerism" column, as [# of chimeras over 80% agouti + # of chimeras under 80% agouti]. In the "Male Germline" column, the numerator of each fraction contains the number of males that sired ES cell-derived progeny, and the denominator is the number of male chimeras tested. This ratio is listed alongside as a percentage.

Additionally, the number and quality of chimeras (judge by coat color) sharply decreased at higher exposures. In contrast, the F1 hybrid v17.2 ES cells were refractory to radiation in terms of their ability to generate strong chimeras that transmit the ES cell-derived genome through the germline. All 9 male chimeras created with cells exposed to 400 RADS produced ES-cell derived progeny. No visible phenotypic abnormalities were observed in chimeras or offspring derived from irradiated ES cells, indicating that the incidence of large chromosomal lesions was relatively low.

To facilitate the construction of targeting vectors specific for any region of the genome, a generic cassette containing adjacent TK and neomycin resistance (neo) genes was made (see Methods). As a first step in generating deficiencies along the t complex of mouse chromosome 17, this TK/neo cassette was integrated into the 129 allele of the D17Aus9 locus by homologous recombination in v17.2 cells. D17Aus9 is under 1 cM proximal to the Brachyury (T) gene, near the centromere. Several clones containing the insert at the target site were obtained, and one (v17.2/1A3) was selected for further experiments after it demonstrated the ability to undergo germline transmission.

To generate deletions encompassing the TK/neo cassette, v17.2/1A3 cells were subjected to 400 RADS of γ-irradiation from a $^{137}$Cs source. Irradiated cells were then selected for loss of TK expression. Prior to irradiation, the cells were maintained in G418-containing medium to prevent the accumulation of cells that lost the cassette by events such as whole chromosome loss or mitotic recombination. 142 colonies survived FIAU treatment. These clones were evaluated for their sensitivity to G418 (G418$^S$), the physical presence of the targeting cassette, and the genotype of two microsatellite markers (D17Mit22 and D17Mit93) at the distal end of the chromosome. 50 of the FIAU resistant (FIAU$^R$) clones retained G418 resistance, suggesting that the TK gene had undergone inactivation by events other than large scale deletion, including transcriptional silencing by methylation. Of the 92 FIAU$^R$/G418$^S$ clones, 26 were analyzed in further detail. Three were missing all distally evaluated 129 alleles, indicating a possible loss of heterozygosity (LOH). In two of these cases, the LOH was caused by mitotic recombination proximal to D17Aus9. The remaining 23 appeared to have true interstitial deletions by analysis of several microsatellite markers along the t complex. Hence, about 88.5% of the colonies identified in the FIAU/G418 selection scheme were true deletions. This extrapolates to a deletion rate of approximately one in 20,000 irradiation survivors. Unirradiated controls yielded FIAU$^R$/G418$^S$ colonies at a frequency 61% lower than those exposed to 400 RADS. However, none of 3 FIAU$^R$/G418$^S$ clones analyzed in detail contained a true deletion, all had apparent LOH.

Twenty-one deletion clones were genotyped at 8 additional microsatellite loci, and by Southern analysis at D17Aus9 and T. This led to the classification of the deletions into 6 categories. All but three lines sustained a deletion of T, indicating that most of the deficiencies were in excess of 0.5 cM. Based on genetic distances listed in the Mouse Genome Database (MGD), these ranged in size from about 1–6 centimorgan. Hence, the current data indicate that the radiation induced deletions average several centiMorgans in length.

Nineteen deletion clones were injected into C57BL/6J blastocysts to generate chimeric mice. Some strong chimeras (as judged by coat color) had short or kinked tails, characteristic of heterozygosity for a mutation at T. Chimeric males were mated to C57BL/6J females, nine cell lines transmitted the deleted chromosome through their germline to date. These results indicate that the majority of cells subjected to the process of irradiation and FIAU selection retain germline competence. Additionally, heterozygosity for deletions was compatible with the birth of live offspring.

The deletions created by this method combine the logistical advantages of ES cells with the nesting of breakpoints characteristic of classical irradiation. Whereas the Cre/LoxP system enables the generation of precise chromosomal deletions (Ramirez Solis et al., Nature 378: 720–724 (1995)), it is technically cumbersome. To create a single deletion, 2 or more successive homologous recombination steps are required, depending on whether chromosomal orientations of the boundary loci are known. In contrast, the irradiation strategy of the present invention enables the creation of an unlimited number of deletions from a single targeted clone. Additionally, the targeting design is simple and generic. In the present invention, nearly 100 unique deletions were created in one experiment at the D17Aus9 locus targeted by the TK-neo selectable marker. This is considerably faster than the several decades over which deletion complexes at visible loci were generated by germ cell irradiation (Rinchik et al., Genetics 137: 845–854 (1994); Russell, Cold Spring Harbor Symp. Quant. Biol. 16: 327–336 (1951)). Additionally, the use of ES cells enables deletions to be selected anywhere in the genome, thereby overcoming the restriction to phenotypically visible loci such as coat color genes. Finally, F1 ES cells allow a determination of the targeted parental chromosome. The deletions in these experiments were created on the paternally derived chromosome (129) of the v17.2 cells, thereby avoiding potential problems with deficiency of the imprinted T maternal effect locus (Tme) in chimeras. Failure to inherit a maternal copy of this gene results in embryonic or postnatal lethality. Mouse genome imprinting information can therefore guide targeting strategies for generating deletions on various chromosomes.

This strategy to create targeted deletion complexes should be an important tool for generating large numbers of unique deletions in order to carry out a functional analysis of the mouse genome. Particular deletions from a set can be crossed in various combinations to create animals homozygous for deletions of different regions. This approach has been used to define functional units within the albino deletion complex. However, a drawback to isolated deletion complexes is that homozygous deficiency for genes closest to the marker locus (a coat color gene, for example) can obscure the phenotypes of distally deleted genes. The strategy described here enables the systematic creation of sets of unique deletions centered at multiple intervals along a chromosome. In this scenario, some deletions from adjacent complexes and hence their associated deficiencies will overlap. Therefore, compound heterozygotes can be generated that contain homozygous deletions of small intervals in between. In this fashion, the function of genes along a chromosome can be systematically evaluated. Deletions produced by this method should have a variety of additional applications. A resource of deletions would expedite complementation analyses and positional cloning of existing mutations or complex trait loci. Mouse models of human deletion syndromes could be generated, and conversely, deletions could be used to delimit regions responsible for phenotypes of trisomies, such as the mouse Down syndrome model. Finally, deletions can be coupled with ENU mutagenesis to saturate a particular chromosomal subregion with point mutations. As the genome project generates large scale DNA sequence data and delineates the position of genes along chromosomes, it will be simpler to ascribe deletion phenotypes to specific genes. systematic construction of deletion complexes as described here, or randomized adaptations on a genome-wide scale, should thereby accelerate functional analysis of the genome in a comprehensive way.

We claim:

1. A method for producing deletions in the chromosomal DNA of a hybrid embryonic stem cell, comprising:
   a) introducing into a hybrid embryonic stem cell a DNA construct, the DNA construct being capable of integrating into the chromosomal DNA by homologous recombination, wherein said hybrid embryonic stem cell is produced from an $F_1$ embryo produced by mating parents from two different lines of the same species;
   b) selecting a hybrid embryonic stem cell from step a) having said construct integrated into its chromosomal DNA;
   c) irradiating the embryonic stem cell selected in step b) to induce deletions in its chromosomal DNA; and d) selecting a stem cell produced in step c) in which at least a portion of the DNA construct, and surrounding chromosomal DNA, has been deleted.

2. The method of claim 1, wherein the DNA construct contains either a selectable marker or a selectable marker flanked on its 5' and 3' ends with DNA fragments which are homologous to a predetermined chromosomal target site.

3. The method of claim 2, wherein the selectable marker is selected from the group consisting of the Herpes Simplex Virus thymidine kinase gene, the neomycin phosphotransferase gene, the hygromycin B phosphotransferase gene, the O-Demethylpuromycin O-Methyltransferase gene and the hypoxanthine-guanine phosphoribosyl transferase gene.

4. A method for producing a non-human multicellular organism having a deletion in its chromosomal DNA, comprising:

a) introducing into a hybrid embryonic stem cell a DNA construct, the DNA construct being capable of integrating into the chromosomal DNA by homologous recombination, wherein said hybrid embryonic stem cell is produced from an $F_1$ embryo produced by mating parents from two different lines of the same species;

b) selecting a hybrid embryonic stem cell from step a) having said construct integrated into its chromosomal DNA;

c) irradiating the embryonic stem cell selected in step b) to induce deletions in its chromosomal DNA;

d) selecting a stem cell produced in step c) in which at least a portion of the DNA construct, and surrounding chromosomal DNA, has been deleted;

e) inserting the hybrid embryonic stem cell selected in step d) into a blastocyst, or aggregating the hybrid embryonic stem cell selected in step d) to a morula, wherein said blastocyst or morula is of the same species as said hybrid embryonic stem cell, thereby generating a chimeric multicellular embryo;

f) introducing the chimeric multicellular embryo of step e) into a host of the same species, whereby a viable multicellular organism develops; and g) deriving offspring of the chimeric multicellular organism of step f) which inherit the deletion of step d).

5. The method of claim 4, wherein the hybrid embryonic stem cell is a mammalian cell.

6. The method of claim 4, wherein the DNA construct contains either a selectable marker or a selectable marker flanked on its 5' and 3' ends with DNA fragments which are homologous to a predetermined chromosomal target site.

7. The method of claim 6, wherein the selectable marker is selected from the group consisting of the Herpes Simplex Virus thymidine kinase gene, the neomycin phosphotransferase gene, the hygromycin B phosphotransferase gene, the O-Demethylpuromycin O-Methyltransferase gene and the hypoxanthine-guanine phosphoribosyl transferase gene.

8. The method of claim 4, wherein the chimeric multicellular organism is a mouse.

* * * * *